United States Patent
Kord

(10) Patent No.: US 11,037,423 B2
(45) Date of Patent: Jun. 15, 2021

(54) POSTURE MONITOR

(71) Applicant: Ali Kord, Los Angeles, CA (US)

(72) Inventor: Ali Kord, Los Angeles, CA (US)

( * ) Notice: Subject to any disclaimer, the term of this patent is extended or adjusted under 35 U.S.C. 154(b) by 407 days.

(21) Appl. No.: 15/762,518

(22) PCT Filed: Sep. 23, 2016

(86) PCT No.: PCT/US2016/053591
§ 371 (c)(1),
(2) Date: Mar. 22, 2018

(87) PCT Pub. No.: WO2017/053899
PCT Pub. Date: Mar. 30, 2017

(65) Prior Publication Data
US 2020/0237292 A1 Jul. 30, 2020

Related U.S. Application Data

(60) Provisional application No. 62/222,594, filed on Sep. 23, 2015, provisional application No. 62/371,083, filed on Aug. 4, 2016.

(51) Int. Cl.
| | |
|---|---|
| *B60Q 1/00* | (2006.01) |
| *G08B 21/04* | (2006.01) |
| *G08B 21/06* | (2006.01) |
| *A61B 5/00* | (2006.01) |
| *A61B 5/01* | (2006.01) |

(Continued)

(52) U.S. Cl.
CPC ........ *G08B 21/0446* (2013.01); *A61B 5/0002* (2013.01); *A61B 5/0077* (2013.01); *A61B 5/01* (2013.01); *A61B 5/1071* (2013.01); *A61B 5/1116* (2013.01); *A61B 5/4809* (2013.01); *A61B 5/6831* (2013.01); *A61B 5/6893* (2013.01); *A61B 5/742* (2013.01); *A61B 5/7405* (2013.01); *A61B 5/746* (2013.01); *G08B 21/06* (2013.01); *A61B 2503/22* (2013.01); *A61B 2560/0223* (2013.01); *A61B 2562/0219* (2013.01); *A61B 2562/0271* (2013.01)

(58) Field of Classification Search
CPC ... A61B 5/4809; A61B 5/0002; A61B 5/0077; A61B 5/01; A61B 5/1071; A61B 5/1116; A61B 5/6831; A61B 5/6893; A61B 5/7405; A61B 5/742; A61B 5/746; A61B 2503/22; A61B 2560/0223; A61B 2562/0219; G08B 21/0446
USPC ........................................................ 340/439
See application file for complete search history.

(56) References Cited

U.S. PATENT DOCUMENTS

| | | | | |
|---|---|---|---|---|
| 4,796,919 A | * | 1/1989 | Linden | B60R 22/024 280/808 |
| 4,832,367 A | * | 5/1989 | Lisenby | B60R 22/024 24/265 R |

(Continued)

*Primary Examiner* — Zhen Y Wu
(74) *Attorney, Agent, or Firm* — GSS Law Group; Gregory S. Smith; Phillip P. Wagner

(57) ABSTRACT

An example posture monitor embodiment includes a first angle sensor coupled to an upper plate and a second angle sensor coupled to a lower plate rotatably connected to the upper plate. The posture monitor may be coupled to a persons chest and to the persons abdomen below the waist to measure an angle related to the persons posture. The posture monitor may activate an alarm indicator when the measured angle changes by more than a preferred threshold value, indicating a change in the persons posture.

6 Claims, 6 Drawing Sheets

(51) Int. Cl.
*A61B 5/107* (2006.01)
*A61B 5/11* (2006.01)

(56) References Cited

U.S. PATENT DOCUMENTS

| | | | | |
|---|---|---|---|---|
| 5,135,257 | A * | 8/1992 | Short | B60R 22/024 |
| | | | | 280/801.1 |
| 5,201,099 | A * | 4/1993 | Campbell | A44B 11/04 |
| | | | | 24/186 |
| 5,605,380 | A * | 2/1997 | Gerstenberger | B60R 22/024 |
| | | | | 24/170 |
| 5,839,792 | A * | 11/1998 | Baik | B60R 22/024 |
| | | | | 297/483 |
| 6,174,032 | B1 * | 1/2001 | Conaway | B60N 2/265 |
| | | | | 297/483 |
| 6,203,110 | B1 * | 3/2001 | Proteau | B60R 22/024 |
| | | | | 297/482 |
| 6,340,209 | B1 * | 1/2002 | Yamamoto | B60R 22/26 |
| | | | | 297/478 |
| 6,450,576 | B1 * | 9/2002 | Rhein | B60N 2/2806 |
| | | | | 297/250.1 |
| 6,750,764 | B1 * | 6/2004 | Henninger | B60R 22/48 |
| | | | | 280/735 |
| 7,445,245 | B2 * | 11/2008 | Beczkowski | B60R 22/00 |
| | | | | 280/801.1 |
| 7,466,221 | B1 * | 12/2008 | Lehr | B60R 22/48 |
| | | | | 340/457.1 |
| 8,146,946 | B1 * | 4/2012 | Emond | B60R 22/30 |
| | | | | 280/801.1 |
| 9,452,341 | B2 * | 9/2016 | Watanabe | A63B 71/06 |
| 9,597,015 | B2 * | 3/2017 | McNames | A61B 5/1121 |
| 2004/0239093 | A1 * | 12/2004 | Eichwald | B60R 22/28 |
| | | | | 280/805 |
| 2008/0203806 | A1 * | 8/2008 | Hibata | B60R 22/40 |
| | | | | 297/478 |
| 2009/0051531 | A1 * | 2/2009 | Boss | G06F 21/88 |
| | | | | 340/568.1 |
| 2009/0105551 | A1 * | 4/2009 | Kelch | F16M 11/2078 |
| | | | | 600/300 |
| 2009/0303208 | A1 * | 12/2009 | Case, Jr. | G06F 1/1616 |
| | | | | 345/204 |
| 2010/0020366 | A1 * | 1/2010 | Iwaki | H04N 1/00689 |
| | | | | 358/474 |
| 2011/0027082 | A1 * | 2/2011 | Herpin | B64C 27/72 |
| | | | | 416/1 |
| 2011/0028865 | A1 * | 2/2011 | Luinge | A61B 5/1114 |
| | | | | 600/595 |
| 2013/0060517 | A1 * | 3/2013 | Sanchez | H01Q 3/04 |
| | | | | 702/151 |
| 2013/0201021 | A1 * | 8/2013 | Limonadi | A63B 21/0407 |
| | | | | 340/573.7 |
| 2014/0176333 | A1 * | 6/2014 | Tsuji | G06F 1/1616 |
| | | | | 340/689 |
| 2015/0022442 | A1 * | 1/2015 | Hwang | G06F 1/1618 |
| | | | | 345/156 |
| 2015/0133821 | A1 * | 5/2015 | Pusch | A61B 5/1122 |
| | | | | 600/595 |
| 2015/0141889 | A1 * | 5/2015 | Ha | A61F 5/0102 |
| | | | | 602/16 |
| 2015/0153312 | A1 * | 6/2015 | Gonzalez | B60B 19/006 |
| | | | | 73/23.2 |
| 2015/0173654 | A1 * | 6/2015 | Belanger | A61B 5/1117 |
| | | | | 600/301 |
| 2015/0247835 | A1 * | 9/2015 | Trovat | G01N 33/24 |
| | | | | 702/2 |
| 2015/0326758 | A1 * | 11/2015 | Kuromatsu | G06F 1/1686 |
| | | | | 348/241 |
| 2015/0374280 | A1 * | 12/2015 | Tomasi | A61B 5/4519 |
| | | | | 600/409 |
| 2016/0085319 | A1 * | 3/2016 | Kim | G06F 3/0487 |
| | | | | 345/156 |
| 2016/0154428 | A1 * | 6/2016 | Senatori | G06F 1/1616 |
| | | | | 361/679.27 |
| 2016/0235489 | A1 * | 8/2016 | Gombert | A61B 34/30 |
| 2017/0161575 | A1 * | 6/2017 | Banno | G06K 9/00342 |
| 2018/0093121 | A1 * | 4/2018 | Matsuura | A63B 21/00185 |
| 2018/0228403 | A1 * | 8/2018 | Li | A61B 5/7455 |

* cited by examiner

POSTURE MONITOR

FIELD OF THE INVENTION

Embodiments are generally related to measurement of angles and more specifically to measurement of angles between parts of a persons body.

BACKGROUND

A person's posture may be an indication of the person's physical health, mental state, or degree of relaxation or fatigue. Some activities, for example driving a car, riding a racing bicycle at high speed, weightlifting, golf, and many others, may have preferred postures for enhancing safety, maintaining good health, or improving performance. It may therefore be important to compare posture to a preferred posture and detect deviations from the preferred posture. However, a person's perceptions of his or her posture may be inaccurate or a person may forget to think about posture while engaged in some other activity. For example, a person may tend to slump forward when falling asleep from a seated position. Or, a person may tend to bend at the waist when lifting a heavy object, rather than keeping the back straight and the abdomen pulled in. A person may not be able to assess his or her posture without being monitored by another person or by constantly remembering to adjust to a preferred posture.

SUMMARY

An example of an apparatus embodiment includes an upper plate rotatably joined to a lower plate by a hinge; a first angle sensor attached to the upper plate; a second angle sensor attached to the lower plate; and a processor electrically connected to the first angle sensor and the second angle sensor. The processor may be adapted to measure a relative angle between the first angle sensor and the second angle sensor when the lower plate rotates about the hinge relative to said upper plate, for example when a person bends at the waist with the upper plate stationary relative to the person's chest and the lower plate displaced by motions of the person's abdomen relative to the chest.

An inertial measurement unit is an example of the first angle sensor. An example posture monitor may further include a bidirectional wireless communications transceiver in data communication with the processor. The processor may be adapted to transmit an alarm message over the bidirectional wireless communications transceiver when the processor measures an angular difference between the first angle sensor and the second angle sensor that is greater than a selected threshold value of angular difference. The example posture monitor may further include an alarm indicator activated by the processor when the processor measures an angular difference between the first angle sensor and the second angle sensor that is greater than the selected threshold value of angular difference.

An example posture monitor embodiment may attach to a seat belt, to an article of clothing worn by a person, and/or directly to the person's skin, for example by a temporary, skin-safe adhesive or an elastic band.

An example of a method embodiment includes at least one of the following steps, in any combination or subcombination: coupling an upper plate of a posture monitor to a chest belt portion of a seat belt; attaching a clip coupled to a lower plate of the posture monitor to a lap belt portion of a seat belt; measuring an angle between the upper plate and the lower plate of the posture monitor; and when the angle between the upper plate and the lower plate changes by more than a threshold value of angular change, activating an alarm to alert the person to adjust posture.

The example method embodiment may further include calibrating the posture monitor to a preferred posture. Calibrating may further include setting a threshold value of angular change by recording a deliberate change in posture corresponding to the person bending forward and/or backward. The example method embodiment may include activating the alarm when the measured angle indicates the person has fallen asleep, and may further include transmitting an alarm message to another device.

DESCRIPTION

An example embodiment of a posture monitor measures an angle between two plates, where an upper plate is preferably held stationary relative to a person's chest and the second plate moves in response to motions of a person's abdomen below the waist. The angular difference between the plates when the person is in a preferred posture represents a calibration or reference position for the posture monitor. When the angle between the plates changes by more than a preferred threshold value, the posture monitor may activate an alarm indicator to remind the person to adjust their posture. The threshold value for activating the alarm indicator may correspond to a magnitude of angular change between the plates that indicates the person may have fallen asleep, possibly bending forward from the waist compared to a more upright, alert position. The posture monitor may be calibrated by the recording an angle between the plates for a preferred posture, and setting limits for triggering alarm conditions by deliberately bending forward and backward by amounts corresponding to alarm conditions.

Embodiments of a posture monitor are advantageous for making accurate comparisons between a person's actual posture at any moment and a preferred posture capture during the calibration process. A preferred posture may correspond to an alert posture, for example while driving a car, a safe posture for conducting an activity such as lifting a heavy weight, an efficient posture for a sports activity, for example an aerodynamically efficient riding position on a bicycle, or other postures preferred for health, safety, or performance reasons.

Figure 1:
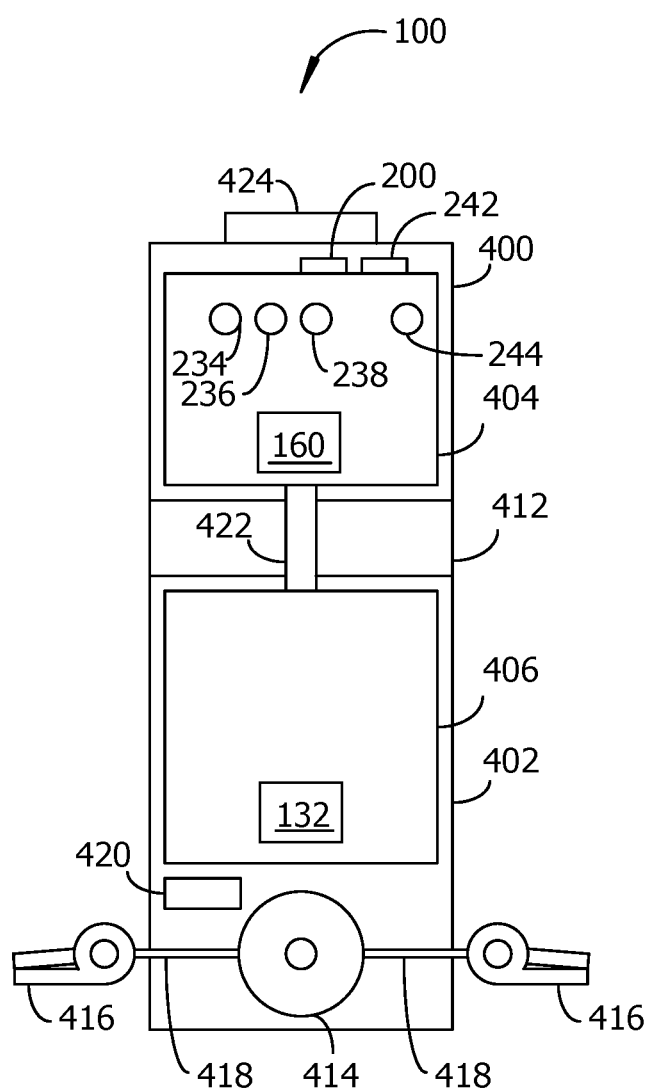
FIG. 1 is a view toward a front side of an example posture monitor.

FIG. 1 and show some features of an example posture monitor apparatus. The example posture monitor 100 includes an upper plate 400 rotatably coupled to a lower plate 402 by a hinge 412. An upper printed circuit board assembly 404 attached to the upper plate includes a first angle sensor 160. An angle sensor may be implemented as an inertial measurement unit. A lower printed circuit board assembly 406 attached to the lower plate includes a second angle sensor 132. An alarm indicator, for example a light emitting diode (LED) 234, may be attached to the upper printed circuit board assembly or alternately to the lower printed circuit board assembly. A charge LED 236 may be provided to indicate that a battery in the posture monitor 100 is being charged. A power LED 238 may be provided to indicate that the posture monitor has been turned on by operation of a power switch 244. Signal and power connections 422 couple the upper printed circuit board assembly to the lower printed circuit board assembly. A control knob 420 attached to a an electrical switch enables a user of the posture monitor 100 to set threshold values for angular values, silence and/or reset alarms, and perform other functions.

A cord reel 414 attached to the lower plate 402 includes two clips 416 extendable outward on cords 418 from opposite sides of the lower plate 402 to attach the plate to a person's clothing, for example a waistband on a skirt or trousers, or to the lap belt portion of a seat belt in a vehicle. A preferred attachment location for the clips 416 causes the lower plate to rotate relative to the upper plate when a person bends at the waist, for example when a person leans forward or backward from a seated or standing position.

Figure 2:
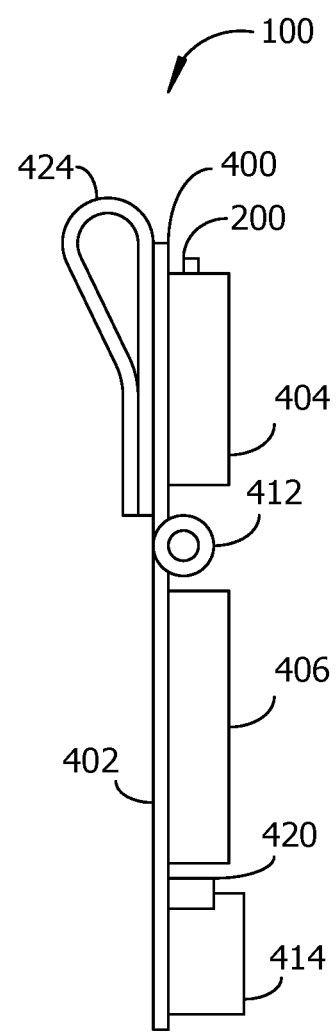
FIG. 2 is a view toward a left side of the example posture monitor of FIG. 1.
Figure 3:
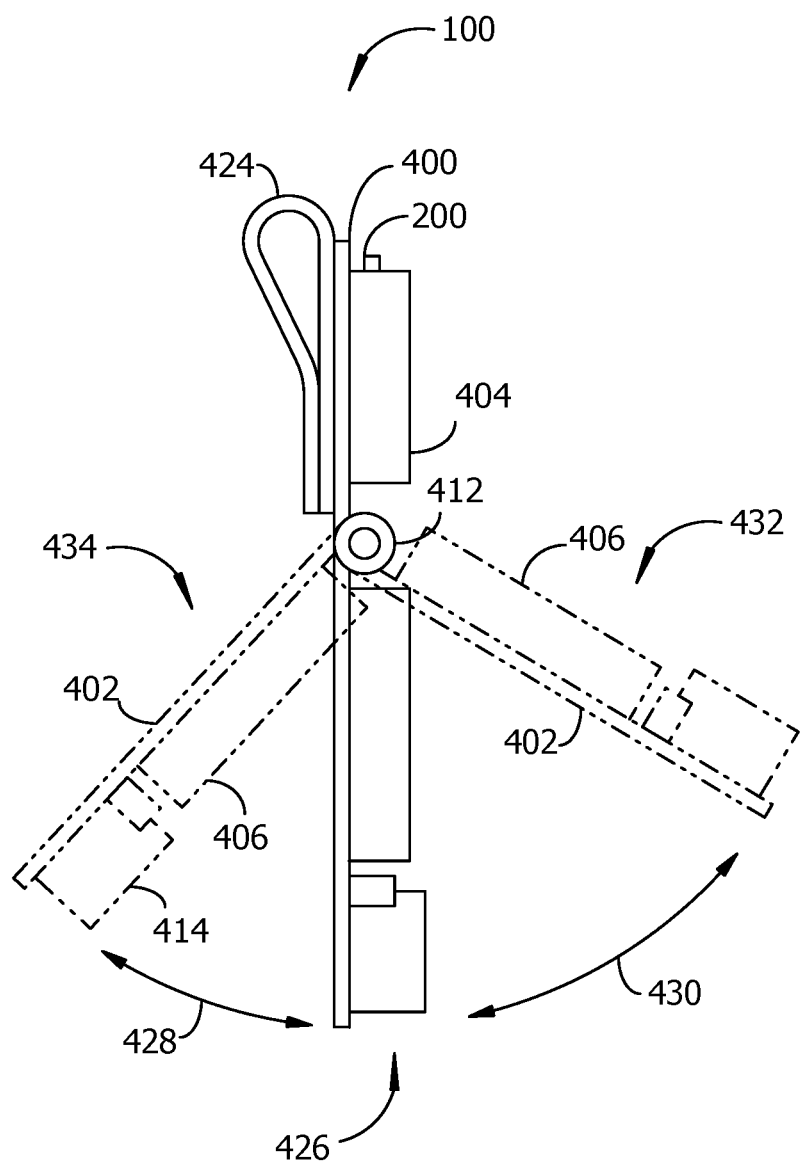
FIG. 3 illustrates examples of relative motions for between the upper plate and the lower plate in the example posture monitor of the previous figures.

As shown in the side view of FIG. 2, an example posture monitor may include a clip 424 positioned on a back surface of the upper plate 400. The clip may be attached to the chest belt portion of a seat belt or to an article of clothing worn by a person. A preferred position for attachment of the upper plate by the clip holds the upper plate stationary relative to the person's chest, with the lower plate rotating relative to the upper plate according to the person's motions as suggested in the example of FIG. 3. IN FIG. 3, the example posture monitor is shown in a neutral position 426, a forward posture position 432, corresponding to a person bending forward at the waist through a positive angle 430, and a backward posture position 434, corresponding to a person bending backward from the neutral position 426 through a negative angle 428.

In an alternative embodiment of a posture monitor, the upper plate and lower plate may be joined to one another along a boundary formed from a flexible material. In some embodiments, the upper plate and lower plate are integrally joined to one another, having a flexible section acting as a hinge (a "live hinge") to allow angular deflection of one plate relative to the other. Although the plates shown in the illustrated examples are approximately flat, in alternative embodiments the upper and lower plates may be nonplanar and may have curved edges and possibly curved surfaces. As used herein, "hinge" includes flexible joints such as live hinges and mechanical hinges.

Figure 4:
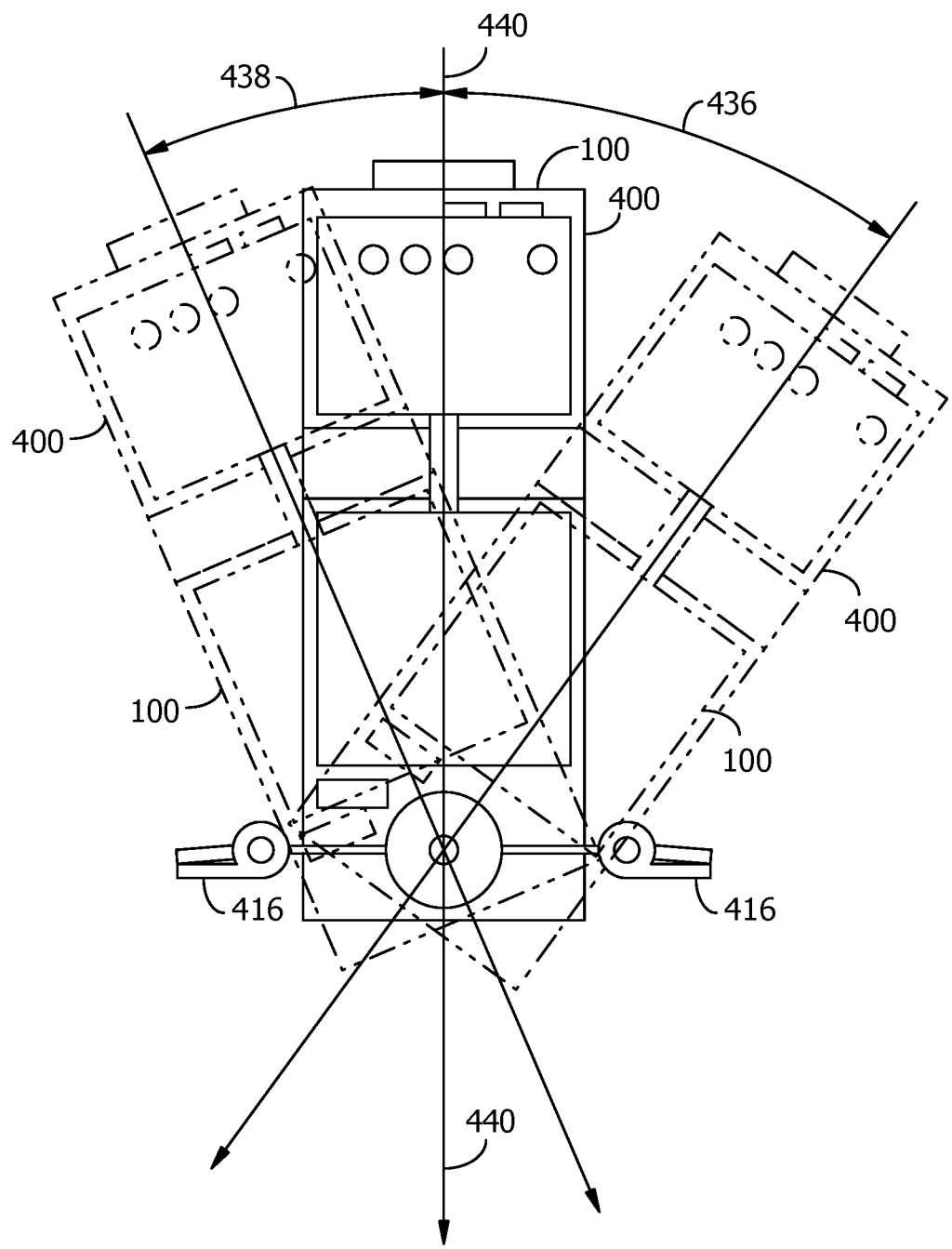
FIG. 4 illustrates examples of lateral rotations of a posture monitor which may be measured and compared to threshold values for angular displacement.

The angle sensors included in an example embodiment of a posture sensor may be capable of detecting lateral rotation angles in addition to the forward- and backward-rotation angle examples of the previous figure. FIG. 4 shows an example of a neutral position in solid lines and laterally rotated positions for an example negative lateral rotation angle 438 and an example positive lateral rotation angle 436. Angles in the example of FIGS. 3-4 may be measured by an angle sensor relative to a vertical direction 440 parallel to a direction of earth's gravity.

Figure 5:
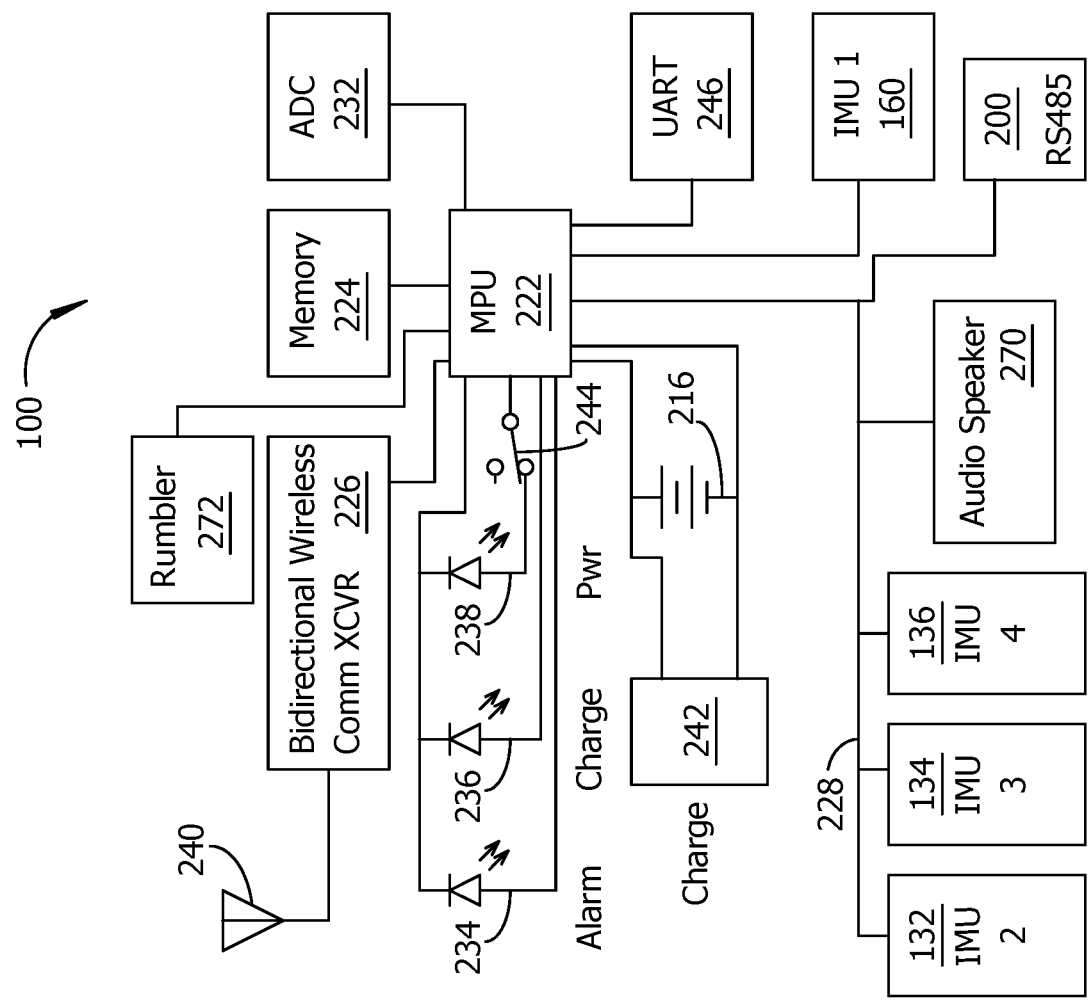
FIG. 5 is a block diagram showing electrical connections between some components of an example posture monitor.

FIG. 5 shows an example of components and electrical connections included in a posture monitor embodiment. A microprocessor (MPU) 222, preferably a processor implemented in hardware by a plurality of semiconductor devices, is electrically connected to a memory 224, a charge connector 242, an electric power storage battery 216, a power switch 244, a first angle sensor 160, and a second angle sensor 132. An alarm indicator coupled to the MPU may include an alarm LED 234 and an audio speaker 270. A vibrating actuator ("rumbler") 272 may be connected to the MPU. The MPU may exchange data and commands with internal and external devices over a UART 246 and/or an RS-485 interface 200.

A posture monitor embodiment may optionally include an analog to digital converter (ADC) 232 coupled to the MPU 222. The posture monitor may include a bidirectional wireless communications transceiver 226 for sending alarm messages to another device, for example to a smart phone or a laptop computer. A posture monitor may optionally include additional angle sensors (134, 136) to record angles between the upper plate and inertial measurement units placed at locations other than a person's abdomen.

Figure 6:
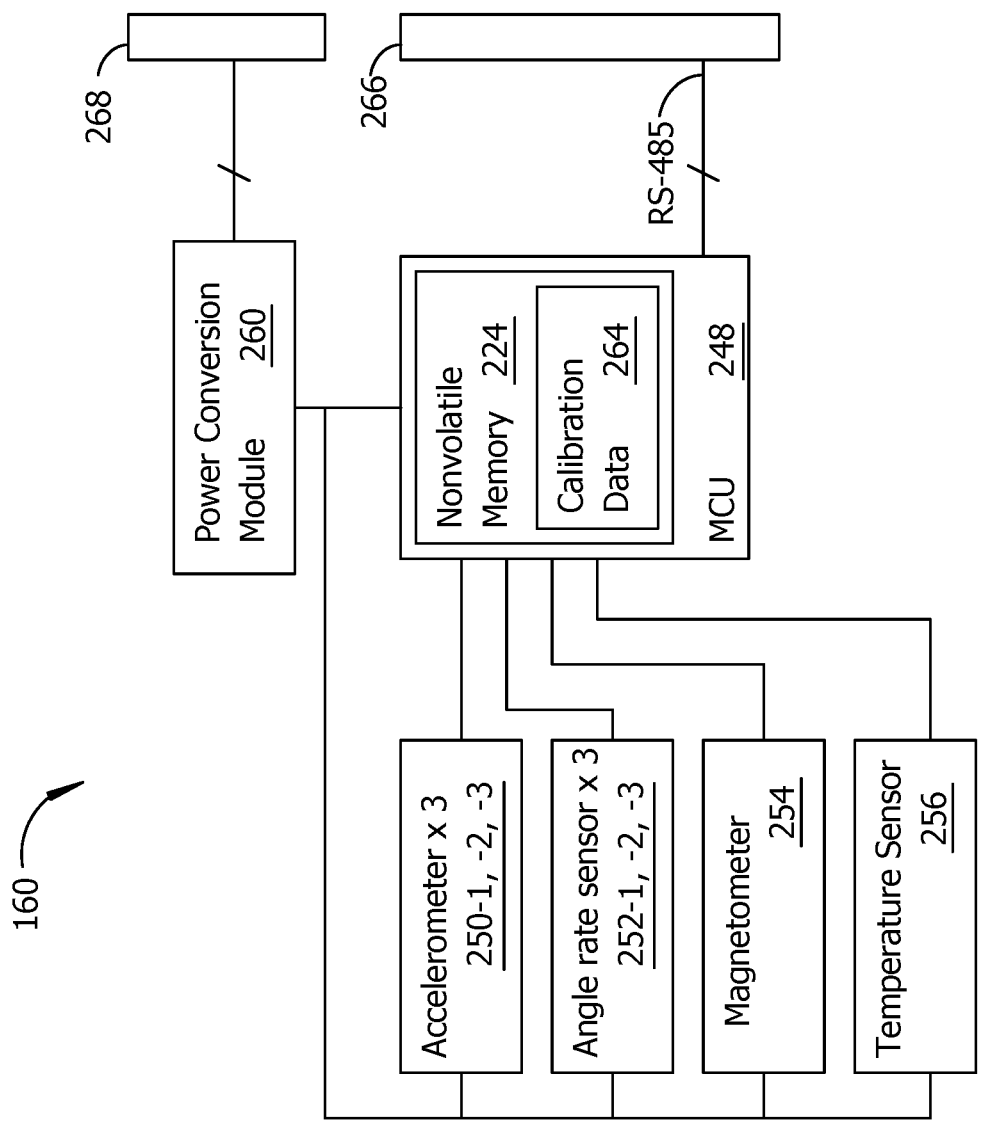
FIG. 6 is a block diagram showing electrical connections between some components of an example angle sensor.
Figure 8:
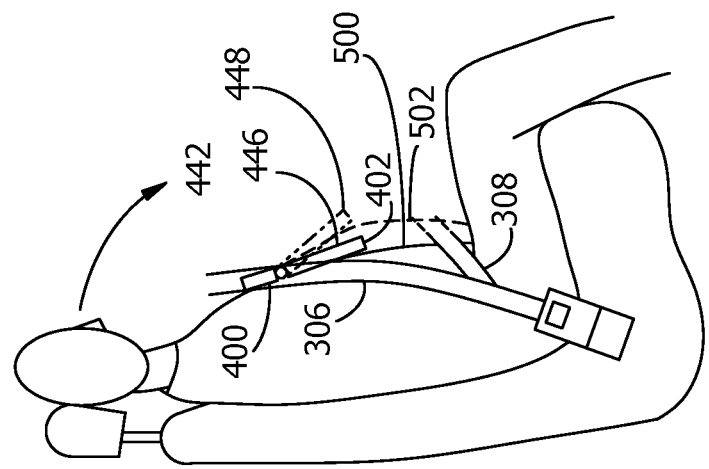
FIG. 8 is a side view of the example of a seated person from FIG. 7, showing an example of a calibrated good posture position for the posture monitor and an example of a poor posture position detected by the posture monitor.
Figure 7:
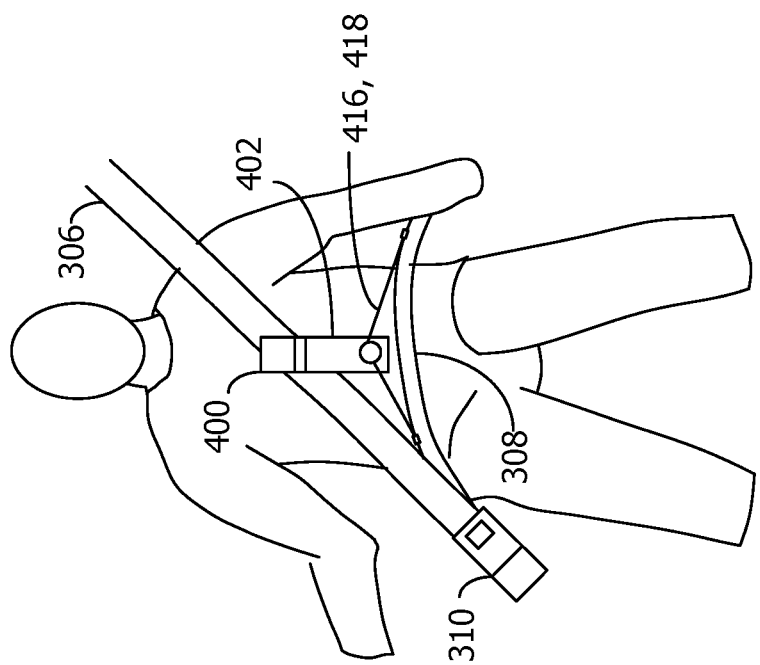
FIG. 7 shows a diagram of a posture monitor coupled to a person to monitor posture, with the upper plate coupled to a chest belt portion of a seat belt that is stationary relative to the person's chest and the lower plate coupled to the person's abdomen by being clipped to the lap belt portion of the seat belt.

FIG. 6 shows an example of an angle sensor 160 implemented as an inertial measurement unit (IMU). The example angle sensor includes a microcontroller (MCU) 248 comprising a nonvolatile memory 224 for holding sensor calibration information 264, a power conversion module coupled to power and ground terminals 268 and to the MCU 248, from one to three accelerometers (250-1, 250-2, 250-3), optionally from one to three angle rate sensors (252-1, 252-2, 252-3), an optional magnetometer 254, and an optional temperature sensor 256 for temperature compensating circuits in the angle sensor. The MCU may communicate with other parts of a posture monitor 100 through an RS-485 interface coupled to data and command input and output terminals 266.

Unless expressly stated otherwise herein, ordinary terms have their corresponding ordinary meanings within the respective contexts of their presentations, and ordinary terms of art have their corresponding regular meanings. An RS-485 connector 200 may be provided to exchange data and/or commands with a processor in the posture monitor. A charge connector 242 may be provided

What is claimed is:

1. A method for monitoring a person's posture by a microprocessor, comprising:
    coupling an upper plate of a posture monitor to a chest belt portion of a seat belt;
    attaching a clip coupled to a lower plate of the posture monitor to a lap belt portion of a seat belt;
    measuring an angle between the upper plate and the lower plate of the posture monitor;
    when the angle between the upper plate and the lower plate changes by more than a threshold value of angular change, activating an alarm to alert the person to adjust posture.

2. The method of claim 1, further comprising calibrating the posture monitor to a preferred posture.

3. The method of claim 1, further comprising setting a threshold value of angular change by recording a deliberate change in posture corresponding to the person bending forward.

4. The method of claim 3, further comprising recording a change in posture corresponding to the person bending backward.

5. The method of claim 1, further comprising activating the alarm when the measured angle indicates the person has fallen asleep.

6. The method of claim 1, further comprising transmitting an alarm message to another device.

* * * * *